(12) United States Patent
Vicenzi et al.

(10) Patent No.: US 12,408,947 B2
(45) Date of Patent: Sep. 9, 2025

(54) EXTERNAL FIXATOR FOR CALCANEUS FRACTURES

(71) Applicant: Orthofix S.R.L., Bussolengo (IT)

(72) Inventors: Federico Vicenzi, Verona (IT); Vincenzo Caiaffa, Bari (IT); Daniele Venturini, Povegliano Veronese (IT)

(73) Assignee: Orthofix S.R.L., Bussolengo (IT)

( * ) Notice: Subject to any disclaimer, the term of this patent is extended or adjusted under 35 U.S.C. 154(b) by 262 days.

(21) Appl. No.: 18/250,488

(22) PCT Filed: Oct. 28, 2021

(86) PCT No.: PCT/EP2021/080024
§ 371 (c)(1),
(2) Date: Apr. 25, 2023

(87) PCT Pub. No.: WO2022/090410
PCT Pub. Date: May 5, 2022

(65) Prior Publication Data
US 2023/0404623 A1    Dec. 21, 2023

(30) Foreign Application Priority Data
Oct. 30, 2020    (IT) .................. 102020000025933

(51) Int. Cl.
*A61B 17/64*    (2006.01)
(52) U.S. Cl.
CPC ................. *A61B 17/6416* (2013.01)
(58) Field of Classification Search
CPC ............ A61B 17/6416; A61B 17/6425; A61B 17/6466; A61B 17/6475; A61B 17/6483
See application file for complete search history.

(56) References Cited

U.S. PATENT DOCUMENTS

| | | | | |
|---|---|---|---|---|
| 2006/0229604 | A1* | 10/2006 | Olsen ................. | A61B 17/6425 606/54 |
| 2010/0222778 | A1* | 9/2010 | Bagnasco ............. | A61B 17/66 606/58 |

(Continued)

FOREIGN PATENT DOCUMENTS

| | | |
|---|---|---|
| EP | 2945553 A1 | 11/2015 |
| IT | UB20159689 A1 | 6/2017 |
| JP | 2004167062 A  * | 6/2004  ......... A61B 17/6425 |

OTHER PUBLICATIONS

English translation of JP-2004167062-A (Year: 2004).*

(Continued)

*Primary Examiner* — Julianna N Harvey
(74) *Attorney, Agent, or Firm* — Haynes and Boone, LLP

(57) ABSTRACT

The present disclosure relates to an external fixator for orthopedic use, in particular for the treatment of calcaneus fractures, comprising: a rigid support for a first clamp for fixing bone screws; a second support for a second clamp that is hinged at an end of the rigid support; a third support for a third clamp that is hinged at an end of the rigid support; the rigid support being configured as a guide with the first clamp slidingly mounted thereon. The fixator according to the invention is made of radiolucent material with joint elements comprising partially radiolucent or radiopaque materials and configured to allow orienting the bone screws held by the clamps in directions that are tilted to each other.

15 Claims, 15 Drawing Sheets

(56) References Cited

U.S. PATENT DOCUMENTS

| 2014/0257288 | A1* | 9/2014 | Chang | A61B 17/645 |
| | | | | 606/59 |
| 2014/0371801 | A1* | 12/2014 | Dall | A61B 17/6441 |
| | | | | 606/86 R |
| 2016/0151099 | A1* | 6/2016 | Olsen | A61B 17/6458 |
| | | | | 606/289 |
| 2017/0209177 | A1* | 7/2017 | Kachooei | A61B 17/6458 |
| 2018/0103987 | A1* | 4/2018 | Mullaney | A61B 17/6475 |

OTHER PUBLICATIONS

European Patent Office International Searching Authority, International Search Report for PCT/EP2021/080024, Dec. 1, 2021, 3 pages.

* cited by examiner

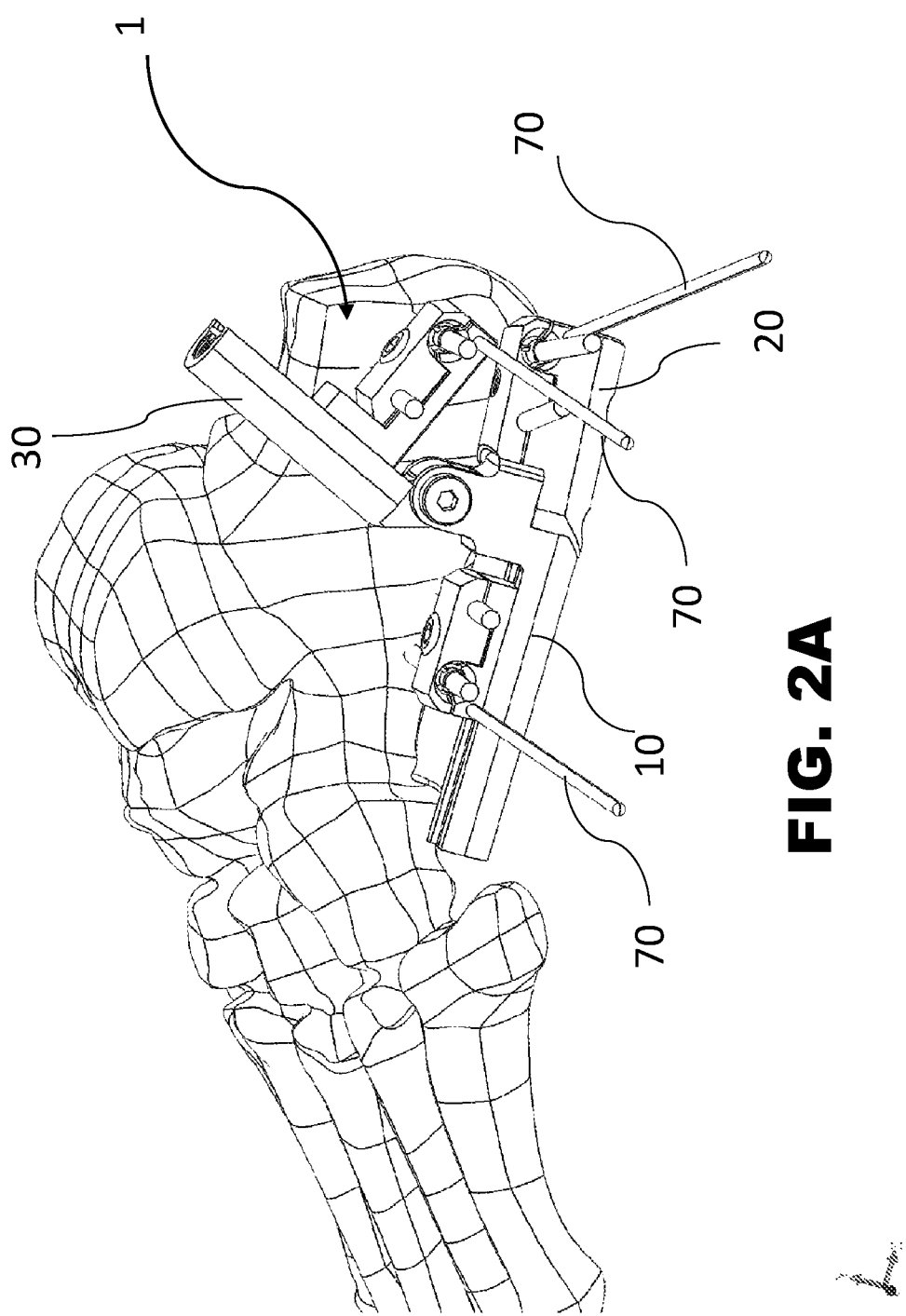

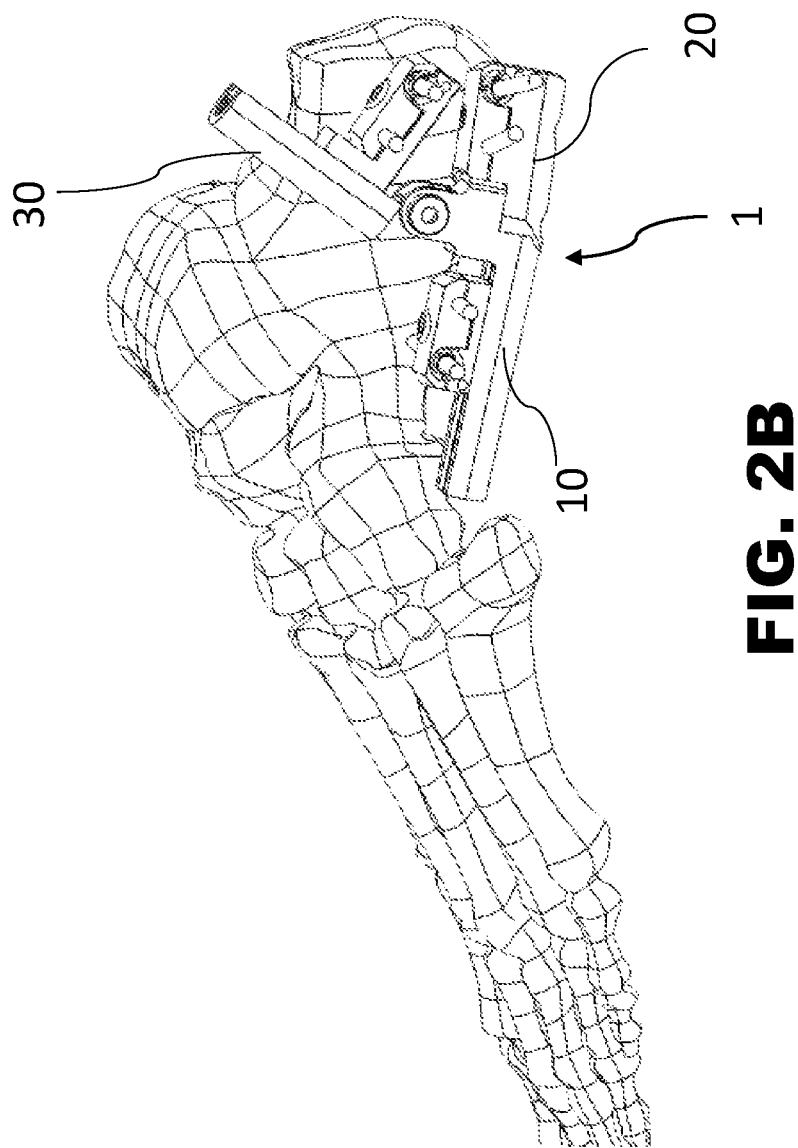

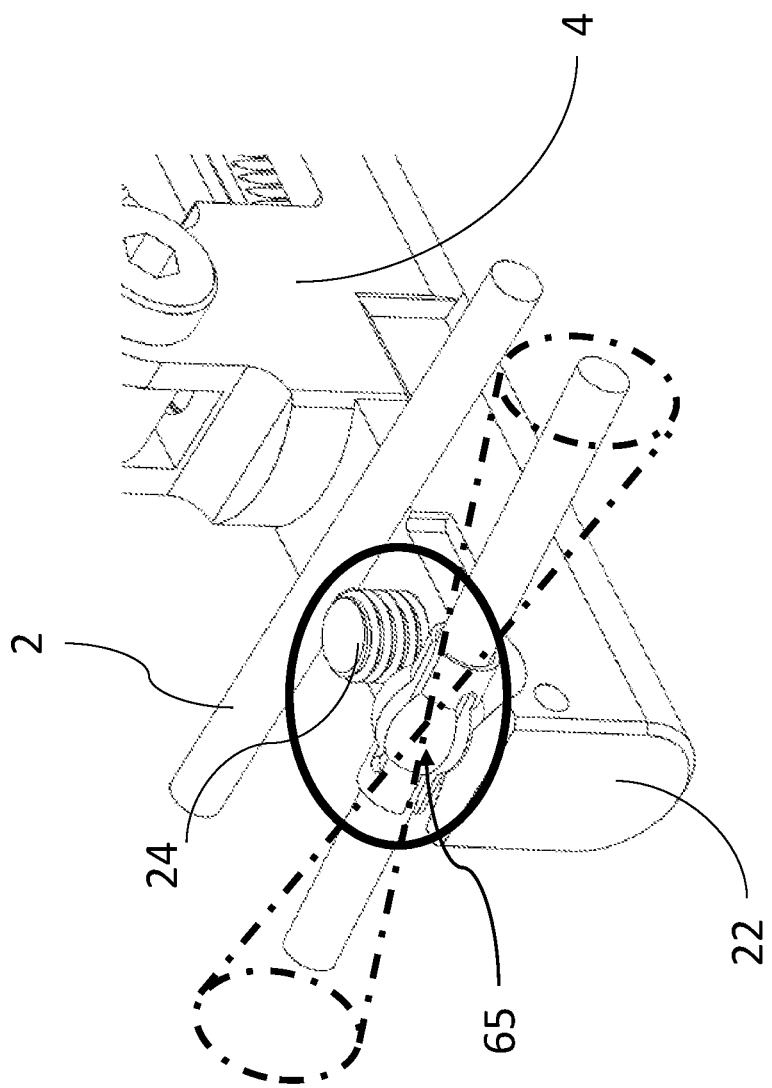

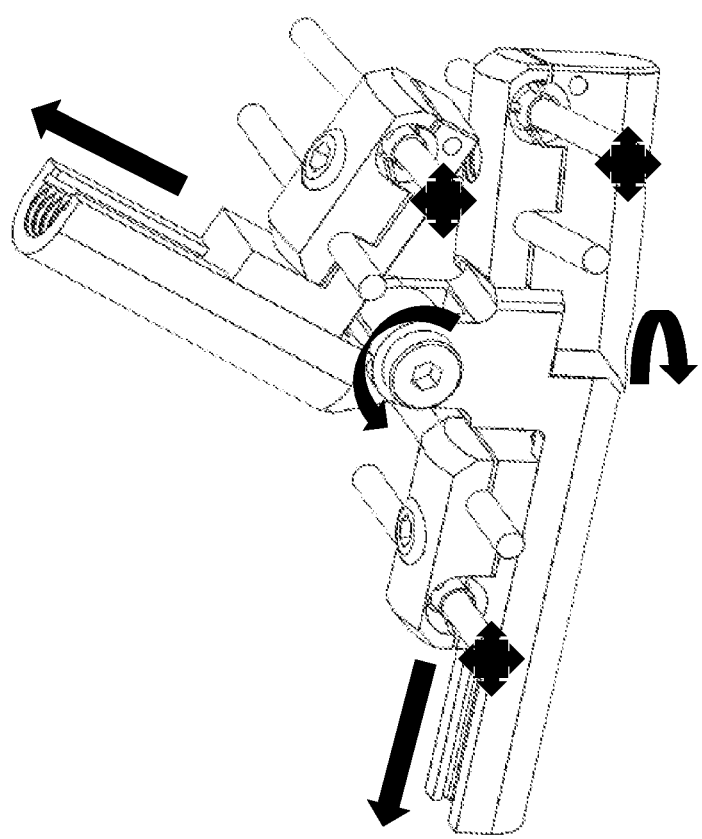

EXTERNAL FIXATOR FOR CALCANEUS FRACTURES

This application is a national phase application of PCT/EP2021/080024, filed Oct. 28, 2021, which claims priority to and the benefit of Italy Application No. 102020000025933, filed Oct. 30, 2020, both of which are incorporated herein in their entireties.

FIELD OF APPLICATION

The present invention relates to an external fixator for orthopedic use, in particular for the treatment of calcaneus fractures.

More particularly, the present disclosure relates to an external fixator comprising at least three clamps for bone screws supported independently of each other.

PRIOR ART

Calcaneus fractures are about 1% or 2% of all fractures that require orthopedic surgery.

In professional literature, the treatment of calcaneus fractures has always been considered a difficult challenge for an orthopedic surgeon. The anatomy and biomechanics of the calcaneus explain the difficulties in treating this type of fractures since the bone is constantly subjected to compressive forces. Indeed the calcaneus works as sesamoid bone in the plantar achilleo-calcaneus system during the execution of the step and is loaded by the body weight; moreover, it has delicate cartilage surfaces that are part of complex joints such as the Chopard and the subtalar.

There are currently two methodologies of approach to calcaneus fractures, and which can be defined conservative or surgical. In the first case, surgery is avoided, and an attempt is made to reduce the fracture from the outside by minimizing manipulation.

However, this methodology has little chances of effective fracture reduction and fixation and often involves a high risk of complications.

In the second case, an open reduction surgical technique is performed with an internal fixation at least in fractures of the II, III and IV type, according to a well-known Sanders classification; however, even this solution is not entirely without risks or complications.

To date, the diatribe between the adoption of a conservative treatment or surgical treatment of this type of fracture remains unsolved since neither of the two methodologies can guarantee good results and the absence of early or late major complications.

In recent years, the so-called minimally invasive surgery is being imposed, which aims at achieving the best functional results by minimizing the access routes and exposure of the calcaneus, while preserving the anatomical structures and the hematoma following the fracture. This technique has led to a decrease in surgical times and related complications.

If the main objective of the treatment of calcaneus articular fractures is the restoration of the three-dimensionality of the calcaneus, with particular regard to the correct alignment on the axial and coronal plane and to the height of the calcaneal body, rather than the reconstruction of the articular congruence of the sub-talus region, the use of a minimally invasive technique of percutaneous reduction and synthesis by means of external fixation appears more than suitable in order to obtain these objectives, also allowing to obtain a stable fixation with a reduced risk of major complications.

The known technique already provides a so-called mini-external fixator comprising three clamps for holding at least six bone screws, two per clamp, and with one of the clamps supported by an arm that can be angularly displaced with respect to the other two clamps to allow the fixation of thalamic fragments.

By using six screws with the external fixator the incidence of screw loosening and the resulting loss of reduction appear to reduce. In some selected cases, the high stability of the device allows early mobilization and an initial partial weight, reducing the risk of stiffness and the healing time.

Although advantageous under various aspects, and substantially satisfying the purpose, this mini-fixator already on the market still has some drawbacks.

First of all, the clamps are rigidly interconnected substantially on a same plane and only one of them can rotate with respect to the other two but always only on the same plane.

Secondly, the calcaneus area is relatively small to be treated, and the use of a mini-fixator also represents an important encumbrance that hinders the surgeon's visualization both during the surgical phase and during subsequent radiographic checks.

Furthermore, the mini-fixators currently available do not allow the screws to be applied independently of each other in the same clamp, making the surgical technique more complex.

Documents IT UB20 159 689 A1 and EP 2 945 553 A1 disclose fixators according to the prior art. In particular, it is observed that the fixator according to IT UB20 159 689 A1 is composed of a main body and two auxiliary bodies hinged thereto, the two hinging axis being parallel to each other.

The technical problem underlying the present invention is to provide a new external fixator for orthopedic use, in particular for the treatment of calcaneus fractures, having structural and functional features such as to overcome the drawbacks of the solutions currently proposed by the prior art.

Such a fixator would allow more suitably treating fractures of at least two if not more fragments of the calcaneus, also allowing a faster reduction of these fractures and an improved restoration of the patient's walking function.

SUMMARY OF THE INVENTION

The solution idea underlying the present disclosure is to provide a rigid structure supporting only one clamp and to articulate the support arms of the other two clamps to this rigid structure so that they are free to be angularly moved independently from each other. Furthermore, at least one clamp is slidingly mounted on the respective support arm.

Based on the above solution idea, the technical problem is solved by an external fixator for orthopedic use, in particular for the treatment of calcaneus fractures, comprising:
  a rigid support for a first clamp for fixing bone screws;
  a second support for a second clamp hinged at an end of the rigid support;
  a third support for a third clamp, which is in turn hinged at an end of the rigid support;
  the rigid support being configured as a guide with the first clamp slidingly mounted thereon.

Advantageously, the end of the rigid support for connection with the second and third supports is configured to house respective hinges having axes that are orthogonal to each other, so as to allow adjusting at will the angle of the second and third supports with respect to the rigid support.

It should be noted that the third support is also configured as a guide with the third clamp sliding thereon.

More particularly, the third clamp is mounted on an "L"-shaped element having a slider base side sliding on the third support and an elevated portion that is perpendicular to the base side whereon a jaw lid of the third clamp is coupled.

The rigid support has a "U"-shaped cross-section, with the valley of the U shape provided with an internal longitudinal thread and the open ends provided with opposite guides; an externally threaded cylindrical carriage is sliding by screwing into the longitudinal thread of the rigid support.

The first clamp has a base with a portion that is projecting downwards to be held in an annular recess formed on said threaded cylindrical carriage.

Furthermore, the rigid support is made of a partially radiolucent material.

This particular conformation is also common to the third support and to the related sliding clamp.

Advantageously, the rigid support and said second and third supports are made of radiolucent material, whereas the hinge elements and the cylindrical carriage are made of partially radiolucent or radiopaque material.

It should also be noted that at least one clamp has a seat for receiving a bone screw that has angular recesses to allow housing the corresponding bone screw in a tilted manner with respect to the other bone screw that is transversally held by the clamp itself.

The seat with angular recesses is the one facing towards the outside of the fixator.

A cage element inserted in the seat with angular recesses to guide and angularly orient a corresponding bone screw into the corresponding angled seat of the clamp is also provided.

Essentially at least one of the clamps has two seats for receiving respective bone screws, one of which is transversal and the other one tilted with respect to the first seat.

In a preferred embodiment the second clamp has a base corresponding to the second support and a removable jaw lid that is mounted on the base by means of a tightening screw coupling.

This tightening screw is inserted in a threaded hole passing through the base portion and the head of the tightening screw is hiddenly received into the base portion of the second support.

Finally, each clamp comprises a respective transversal through-hole placed at one end of the clamp towards the outside of the fixator to house a corresponding K-wire.

The features and advantages of the external fixator according to the present disclosure will become apparent from the following description of an embodiment given by way of non-limiting example with reference to the appended drawings.

BRIEF DESCRIPTION OF THE DRAWINGS

FIG. 2A shows a perspective view of an initial application of the fixator of FIG. 1 and a calcaneus shown by schematic lines;

FIG. 2B shows a perspective view of the final application of the fixator of FIG. 1 and a calcaneus shown by schematic lines;

FIGS. 11 and 12 show respective perspective and schematic views of further and conjugated portions of the clamps constituting the fixator of FIG. 1;

FIG. 15 shows a perspective view of the fixator of FIG. 1 with indicated the handling possibilities represented by arrows.

DETAILED DESCRIPTION

Figure 1:
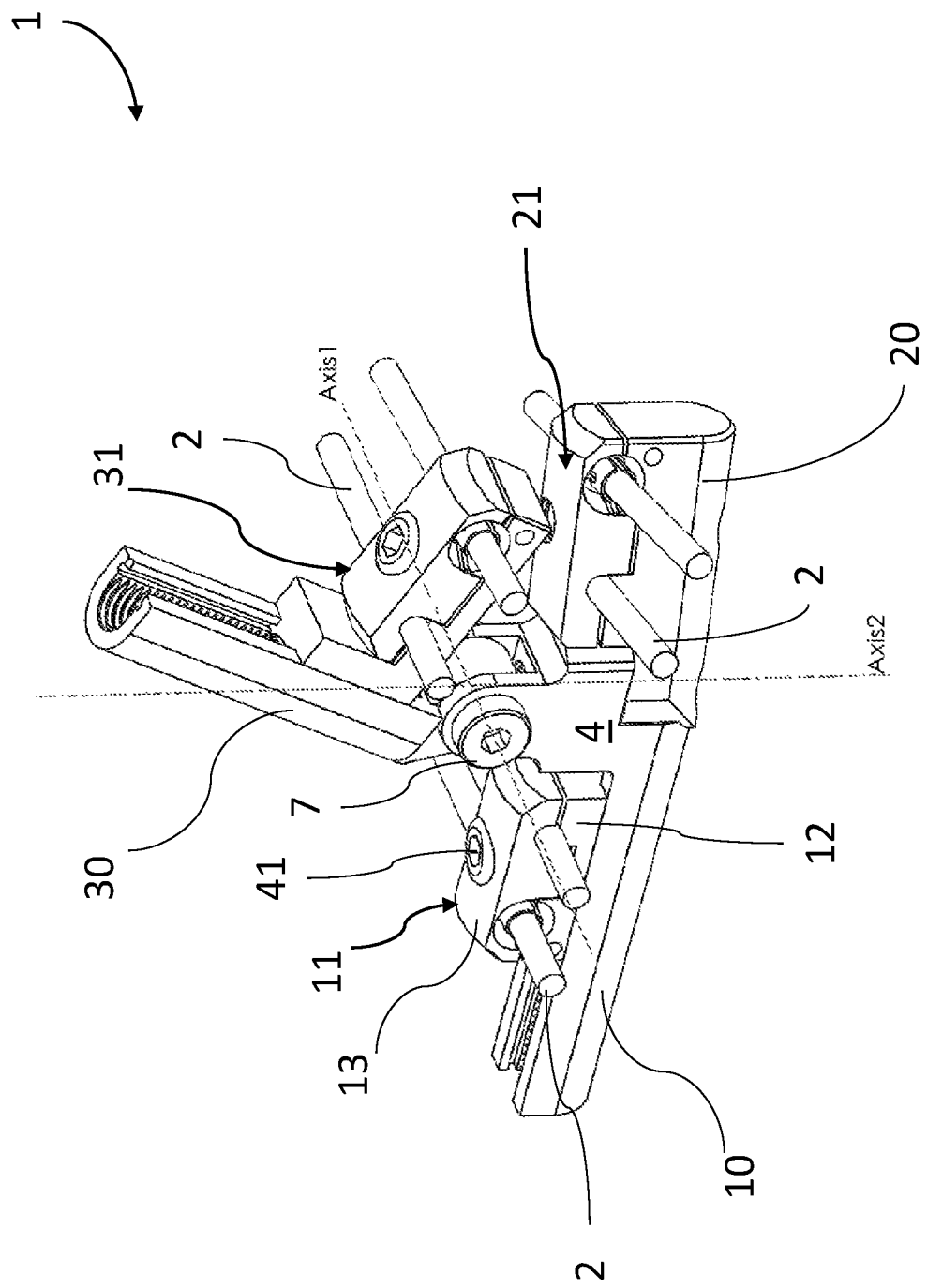
FIG. 1 shows a perspective and schematic view of an external fixator for orthopedic use made according to the present disclosure to treat in particular calcaneus fractures.
Figure 3:
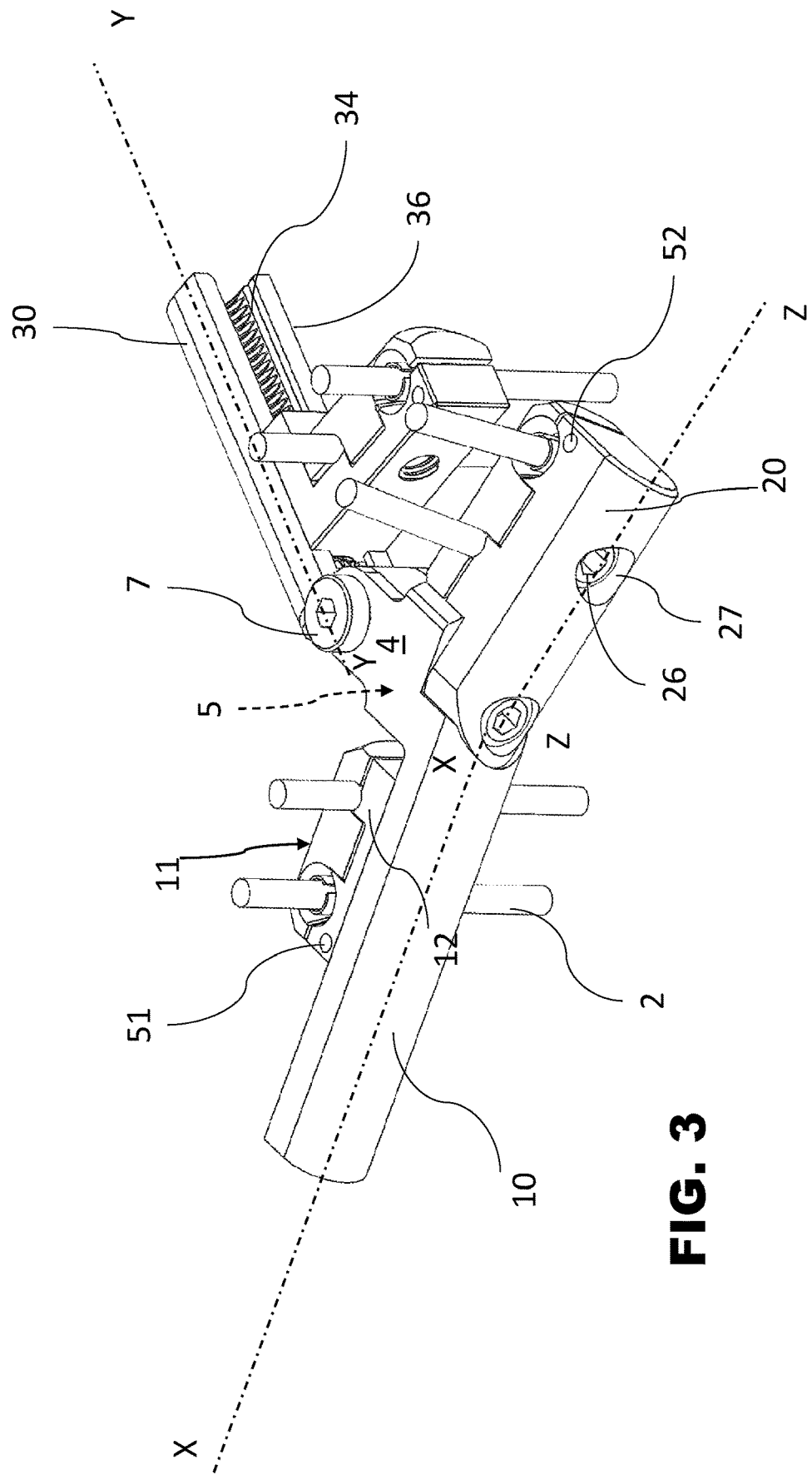
FIG. 3 shows a perspective and schematic view of the fixator of the present disclosure according to a different observation point.

With reference to these figures, reference number 1 globally and schematically indicates an external fixator for orthopedic use made according to the present disclosure for the treatment of calcaneus fractures and any way of the achilleo-calcaneus plantar region.

The fixator 1 comprises three clamps, 11, 21, 31, each intended to receive and hold at least one pair of conventional implanted bone screws 2 of the foot bone.

The fixator 1 comprises a rigid support 10 for a first clamp 11 for holding bone screws 2.

This rigid support 10 is a kind of track section whereon the clamp 11 is mounted sliding as a slider, though it may be constrained in a pre-fixed position along the support 10 by means of a fixing adjustment screw, as it will be seen hereinafter.

Figure 4:
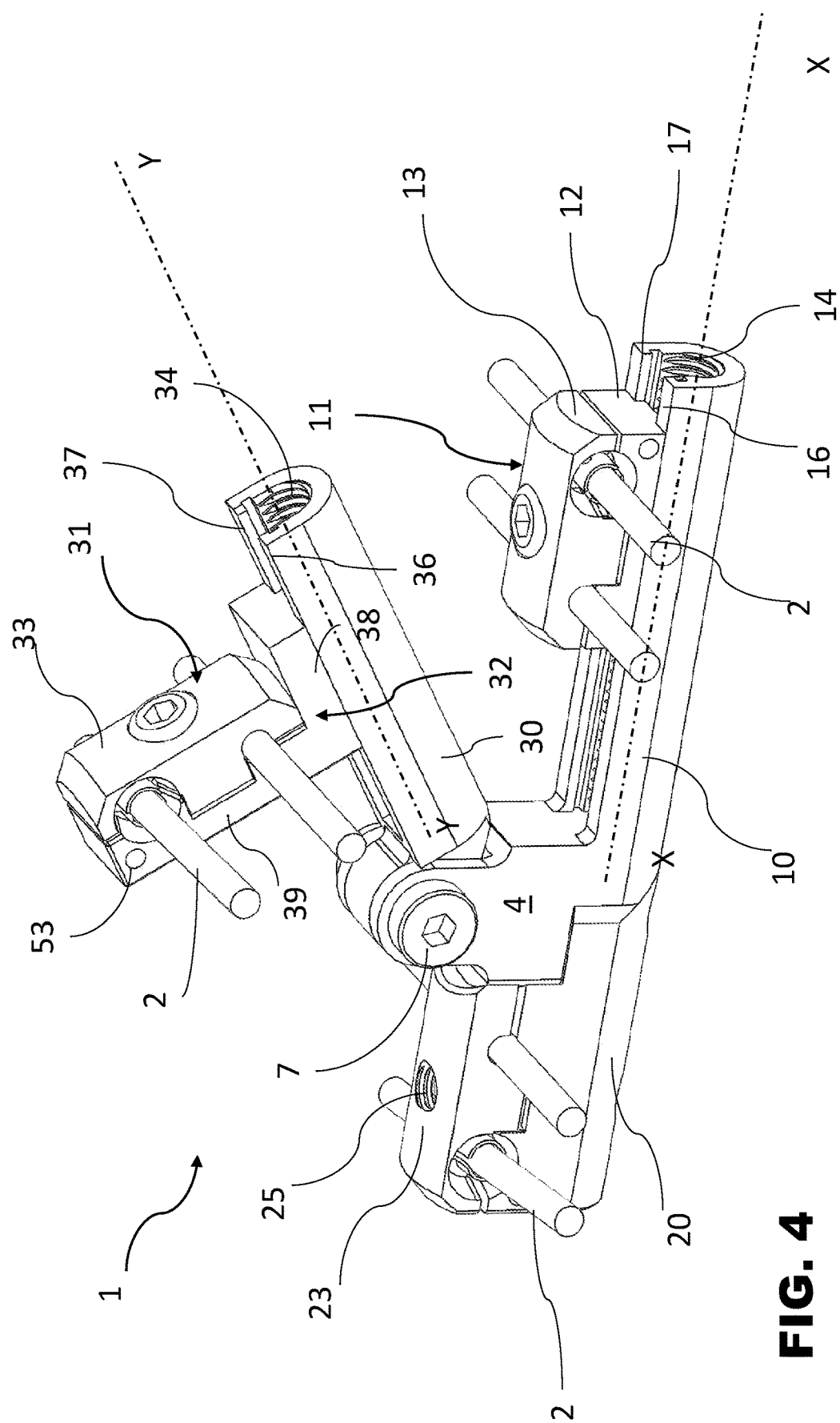
FIG. 4 shows a perspective and schematic view of the fixator of the present disclosure according to a further and different observation point.

More particularly, as shown in FIG. 4, the rigid support 10 has a "U"-shaped cross-section, with the valley of the U provided with an internal longitudinal threading 14 and the open ends provided with opposite guides 16 and 17. In the following description the support 10 extended according to a generic longitudinal axis X-X will be considered.

The first clamp 11 comprises a base 12 mounted sliding on the guides 16 and 17 and a jaw lid 13 on top of the base 12 and holds therewith the transversally extended bone screws 2.

A fixing screw 41 is provided to constrain the jaw lid 13 on the base 12. This screw 41 has an enlarged head with an Allen seat and a threaded stem inserted by screwing in a corresponding hole centrally obtained in the base 12 between the seats for receiving the transversal bone screws 2.

The base 12 del clamp 11 has a central portion 19 protruding downwards to be held in an annular recess 18 centrally formed on a threaded cylindrical carriage 15.

The smooth stem 46 of the screw 44 is received and is rotatable in the hole of the tapered end 55 of the third support 30.

The externally threaded cylindrical carriage 15 is sliding by screwing in the longitudinal threading 14 of the rigid support 10 along the X-X axis. A polygonal-section Allen seat 6 is formed at a free end of the carriage 15 and allows moving the carriage 15 by screwing by means of a maneuvering stem (not shown). The carriage 15 is substantially a sliding screw in the nut screw 14.

Figure 13B:
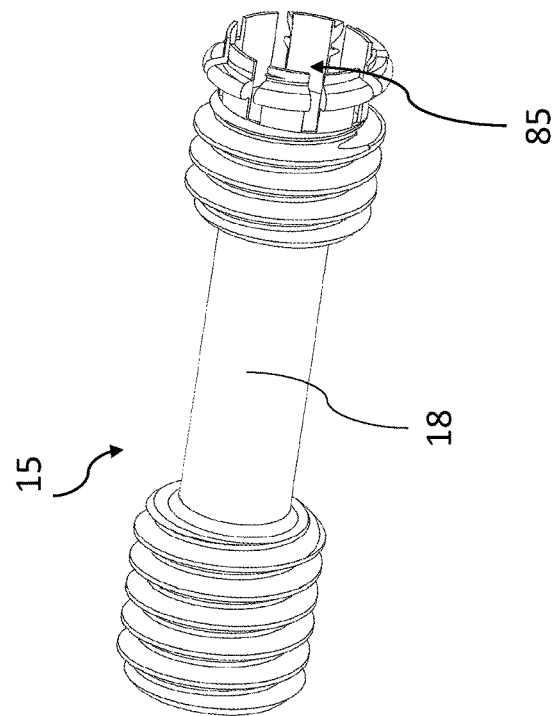
FIGS. 13A and 13B show respective perspective views of internal components of the fixator of FIG. 1.

The carriage 15 is shown in a perspective view in FIG. 13B and comprises at an end thereof 85 an elastic-prong crown that allows generating a friction on the rotation during the advancement. The friction obtained with this elastic interference prevents the free rotation of the screw carriage so that it does not accidentally unscrew, losing its position or preload on the fracture gap.

The annular recess 18 of the carriage 15 supports and holds the central portion 19 of the base 12 which as a whole slides along the guides 16 and 17. Therefore, the advancement or retraction of the cylindrical carriage 15 below the base 12 along the X-X axis of the support 10 also moves the whole clamp 11 in the same axial direction.

Advantageously, a solid end 4 of the rigid support 10 is shaped so as to receive a first joint hinge 5 between the rigid support 10 and a second support 20 for a second clamp 21 for holding bone screws 2.

Figure 5:
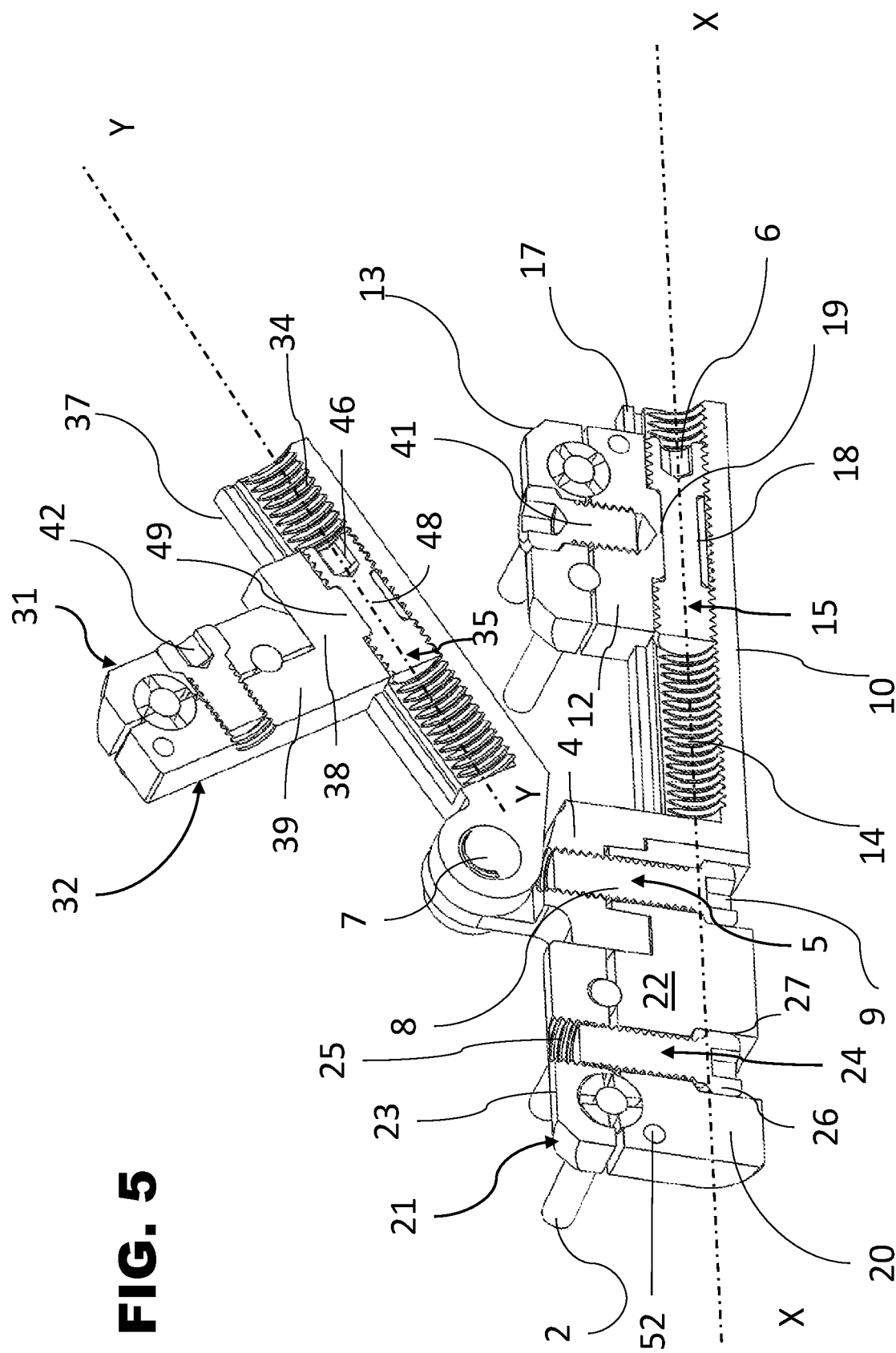
FIG. 5 shows a longitudinal sectional view of the fixator of the present disclosure.

The hinge 5 is visible in the section of FIG. 5 and has the peculiarity of being a screw 8 of non-magnetic material, for instance aluminum, titanium alloy or non-magnetic steel.

A second joint hinge 7 is also provided between the rigid support 10 and a third support 30 for a third clamp 31.

This second hinge 7 is received still in the end solid portion 4 of the rigid support 10 and is extended according to a rotation axis indicated in FIG. 1 as Axis1.

The other joint hinge 5 with the second support is instead extended according to a rotation axis indicated as Axis2, which is orthogonal to the preceding axis Axis1.

The two rotation axes Axis 1 and Axis 2 are orthogonal to each other, as shown in FIG. 1. In particular, the third support has the Y-Y axis normally arranged with respect to the perpendicular to the sliding plane of the first horizontal clamp 11. The side clamp 21 has the hinge 5 that allows the varus-valgus correction and may be rotated even at the end of the surgery once the fixator 1 has already been positioned.

To ensure a high seal of the hinge 5, a conical coupling has been designed, which is forced by a screw, similar to a morse cone, thus creating a stable construction.

This configuration of the hinges 5, 7 allows the second support 20 and the third support 30 to be angularly tiltable with respect to the resting plane of the first rigid support 10 which also the X-X axis belongs to.

In the drawings, Z-Z and Y-Y indicate the longitudinal extension axes of the second 20 and third supports 30, respectively.

Returning to the structure of the second support 20, it should be noted that said second support 20 is shorter than the rigid support 10 being extended along the Z-Z axis by a tract that is smaller than the extension of the first support along own X-X axis.

Thanks to the joint represented by the hinge 5, the second support 20 may be angularly displaced with respect to the resting plane of the first support 10 and the respective X-X and Z-Z axes form an angle between them.

The second clamp 21 comprises a base 22 and a jaw lid 23 on top of the base 22 and holds therewith the transversally extended bone screws 2.

The second support 20 itself represents the base 22 of the second clamp 21 and comprises at an end, which will be defined external, a transversal through-hole 52 to receive a first stabilization Kirschner wire (or K-wire).

A screw 24 with enlarged head 26 having an Allen seat is provided to constrain the jaw lid 23 on the base 22 of the second clamp 21.

The screw 24 is inserted in a threaded hole 25 passing through the base portion 22 and the jaw lid 23 according to a direction orthogonal to the Z-Z axis of the second support 20.

An enlarged portion 27 of the hole 25 hiddenly receives the enlarged head 26 of the screw 24 in the base portion 22 of the second support 20.

Essentially, the head of the fixing screw is hiddenly housed in the base portion 22 of the second support 20 and operated from below.

Figure 6:
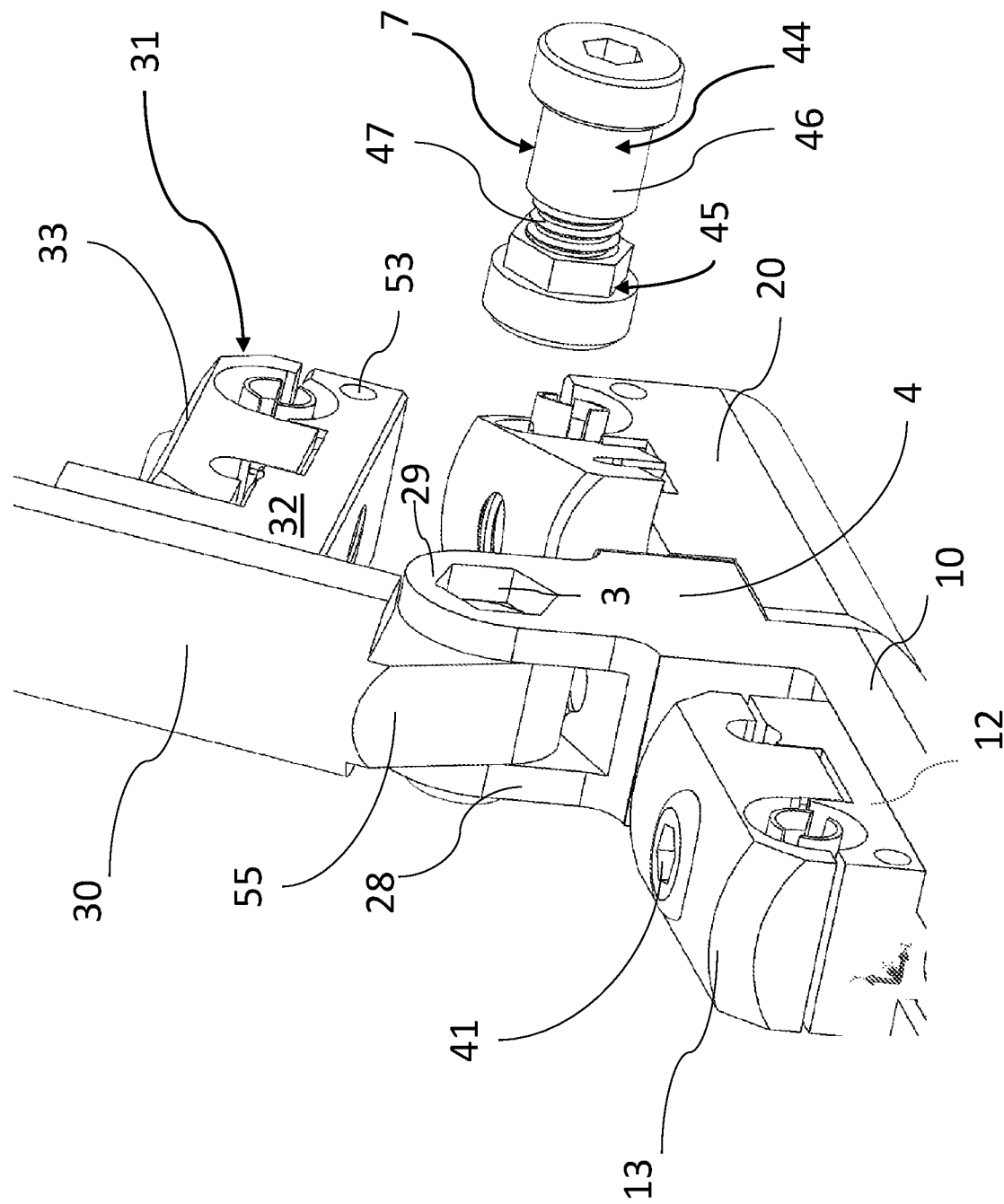
FIG. 6 shows a perspective, schematic and partial view of a central portion of the fixator of the present disclosure.
Figure 7:
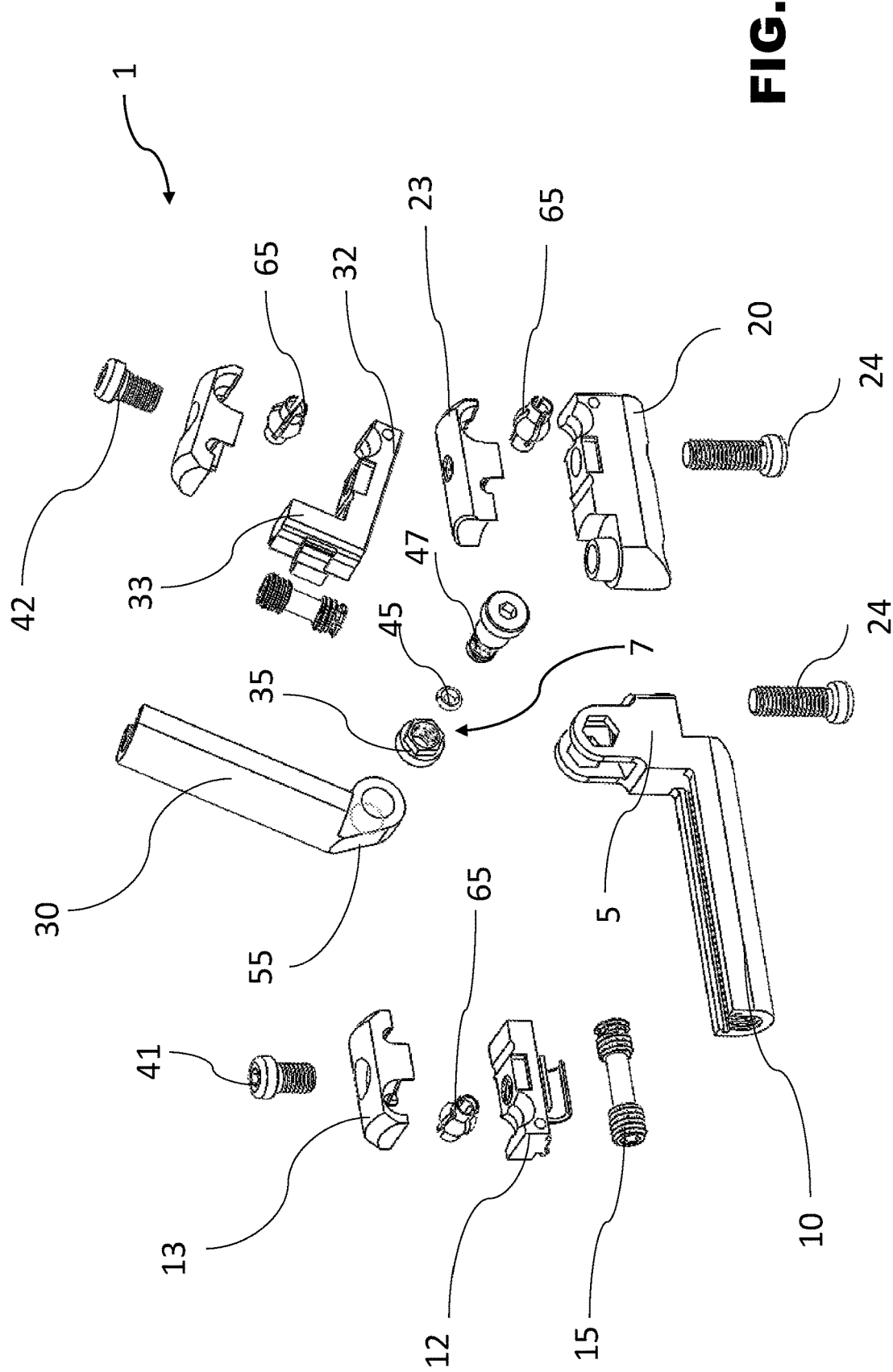
FIG. 7 shows a perspective view in detached parts of the fixator of FIG. 1.

As well shown in FIG. 6, the third support 30 is articulated to the solid end portion 4 of the rigid support 10 by means of the coupling with the hinge 7.

A fork formed by a pair of annular prongs 28, 29 on top of the solid portion 4 holds a tapered and perforated end 55 of the third support 30, also receiving the hinge 7.

The hinge 7 is structured as a kind of bolt having a screw portion 44 with smooth stem 46 and threaded end and a nut 45 that is internally polygonal-shaped, for instance hexagonal. The screw 44 and the nut 45 are coupled by screwing to form the hinge 7 body, with interposition of an elastic element 47.

At least one of the annular prongs 28, 29 has a polygonal shaped hole 3, for instance hexagonal, so as to receive by shape coupling the corresponding nut 45 shape, thus preventing it from rotating in the hole 3.

Advantageously, this conformation of the hinge 7 makes the fixator 1 ambidextrous thanks to the particular design of the screw 44 for blocking the hinge of the third support extended in a tilted direction.

Let us now examine the structure of the third support 30 in greater detail.

The fixator 1 comprises a rigid support 10 for a first clamp 11 for holding bone screws 2.

Analogously to the first support 10, the third support 30 is a kind of track whereon the third clamp 31 is mounted sliding as a slider.

In this case as well, the clamp 31 may be constrained in a pre-fixed position along the third support 30 by means of a fixing adjustment screw, as it will be seen hereinafter.

More particularly, as shown in FIGS. 4 and 5, the third support 30 has a "U"-shaped cross-section, with the valley of the U shape provided with an internal longitudinal threading 34 and the open ends provided with opposite guides 36 and 37. As seen previously, the third support 30 is extended according to a longitudinal Y-Y axis that is oblique to the extension X-X axis of the rigid support 10.

The third clamp 31 comprises a base 32 mounted sliding on the guides 36 and 37 and a jaw lid 33 on top of the base 32 and holds therewith the transversally extended bone screws 2.

Advantageously, the base 32 is "L"-shaped with a slider side 38 of the "L" shape sliding on the guides 36, 37 and the other side 39 that is a perpendicularly extended elevated portion and whereon the jaw lid 33 is coupled.

Therefore, with respect to the first clamp 11 of the rigid support 10, the third clamp 31 of the third support 30 is supported by the portion 39 that is elevated perpendicularly to the direction of the Y-Y extension axis of the third support 30 itself.

A fixing screw 42 is provided to constrain the jaw lid 33 on the elevated portion 39 of the base 32. This screw 42 has an enlarged head with Allen seat and threaded stem inserted by screwing in a corresponding hole centrally obtained in the elevated portion 39 of the base 32 between the seats for receiving the transversal bone screws 2.

The slider portion 38 of the base 32 of the clamp 31 has a central portion 49 protruding downwards to be held in an annular recess 48 centrally formed on a threaded cylindrical carriage 35.

The cylindrical carriage 35 is sliding by screwing in the longitudinal threading 34 of the third rigid support 30 along the Y-Y axis. Said screw carriage 35 has a structure that is totally identical to that of the carriage 15 and is shown in FIG. 13B with the end 85 provided with an elastic-prong crown.

A polygonal-sectioned Allen seat 46 is formed at a free end of the carriage 35 and allows moving the carriage 35 by screwing by means of a maneuvering stem (not shown). The carriage 35 is substantially a sliding screw in the nut screw 34.

The annular recess 48 of the carriage 35 supports and holds the central portion 49 of the slider base 32, which as a whole is sliding along the guides 36 and 37. Therefore, the advancement or retreat of the cylindrical carriage 35 below the slider base 32 along the Y-Y axis of the third support 30 also moves in the same axial direction along the third clamp 31.

In a preferred embodiment, the supporting structure of the fixator 1 is made of radiolucent material for instance of a composite material, (for instance Peek or Ultem) loaded with carbon fiber.

Load-bearing structure indicates both the rigid support 10 and the second and third supports 20 and 30, as well as the clamps 11, 21 and 31.

Moreover, even the structure of the hinges 5 and 7 and/or of the screws 15 and 35, which allow the clamps 11 and 31 to slide, may be made of an X-rays partially transparent material, such as for instance aluminum.

Figure 9:
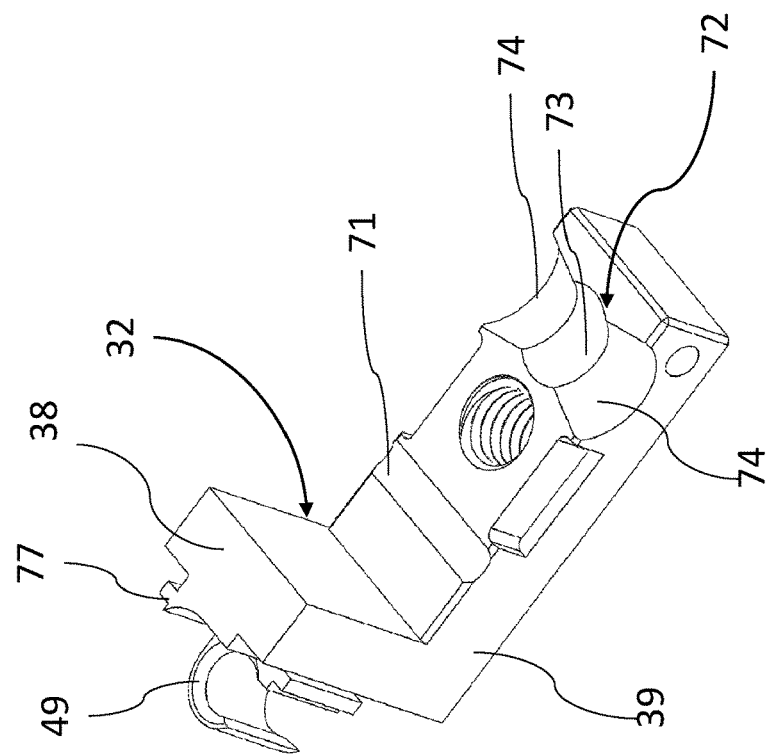
FIGS. 8, 9 and 10 show respective perspective and schematic views of portions of clamps constituting the fixator of FIG. 1.
Figure 8:
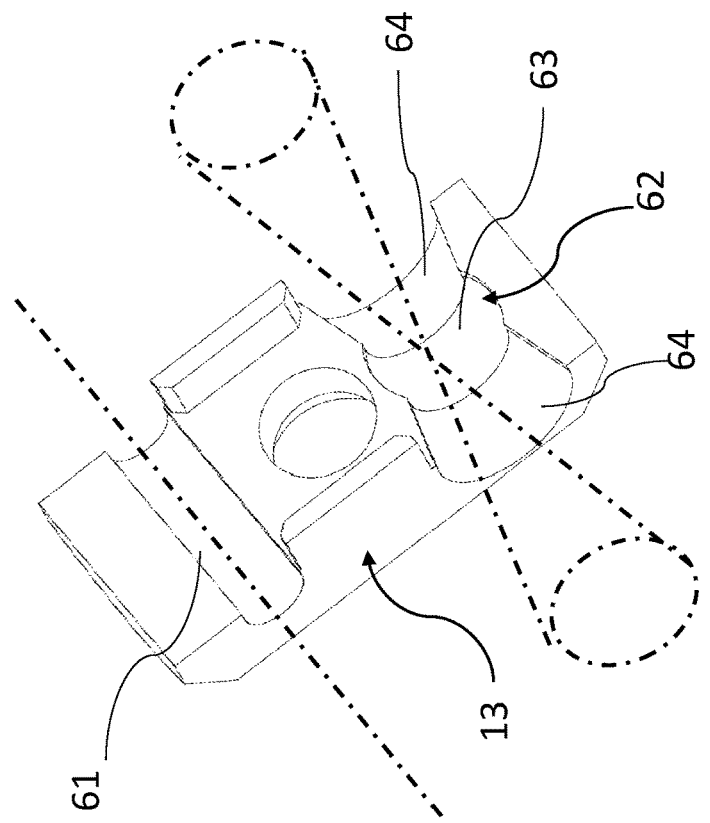
Figure 10:
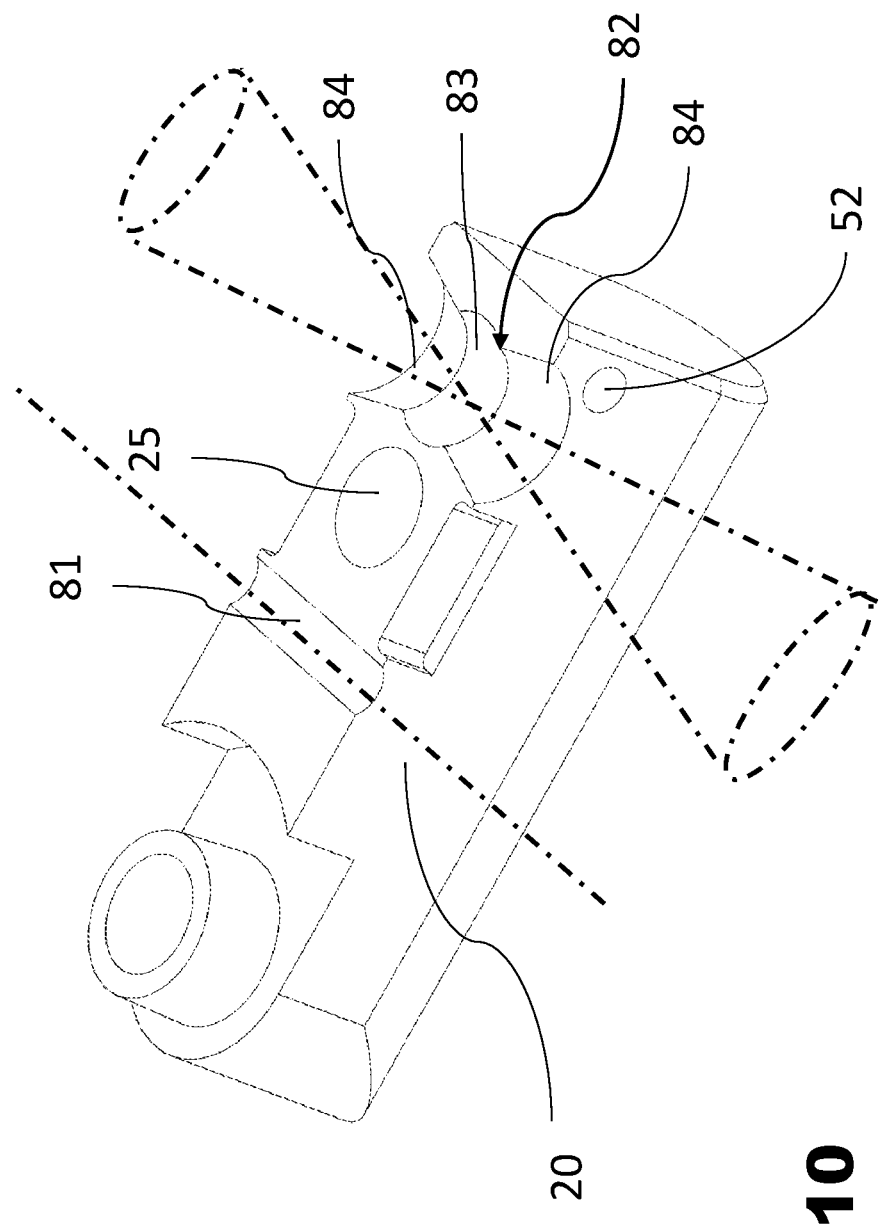

Now, with particular reference to the examples of FIGS. 8, 9 and 10, the housing seats of the bone screws 2 extended transversally in each clamps 11, 21 or 31 are described in greater detail.

FIG. 8 shows in a perspective view the internal surface of the jaw lid 13 of the first clamp 11. From this figure it can be observed how a seat 61 for bone screw is conventionally configured as a semi-circular section channel whereas the other seat 62 is instead shaped with angular recesses.

More particularly, the seat 62 comprises an almost hemispherical-shaped central portion 63 joined with two opposite flared and semi conical-shaped seats 64.

This set of shaped seats 63, 64 defines and delimits with corresponding and joined shaped seats formed in the other base component 12 of the clamp 11 a maneuvering space schematized by the double cone identified by the dotted lines in FIG. 8.

A small cage 65 for holding a bone screw 2 is housed in this maneuvering space which helps angularly positioning the bone screw located in the outermost seat of the clamp with respect to the central body of the fixator 1.

Figure 13A:
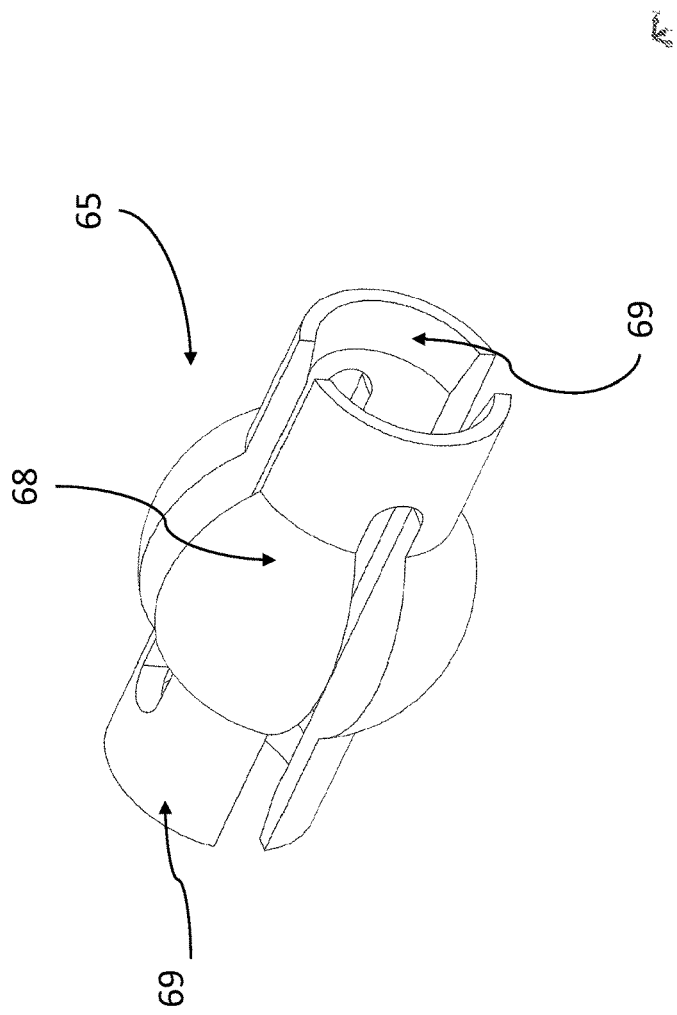
Figure 14:
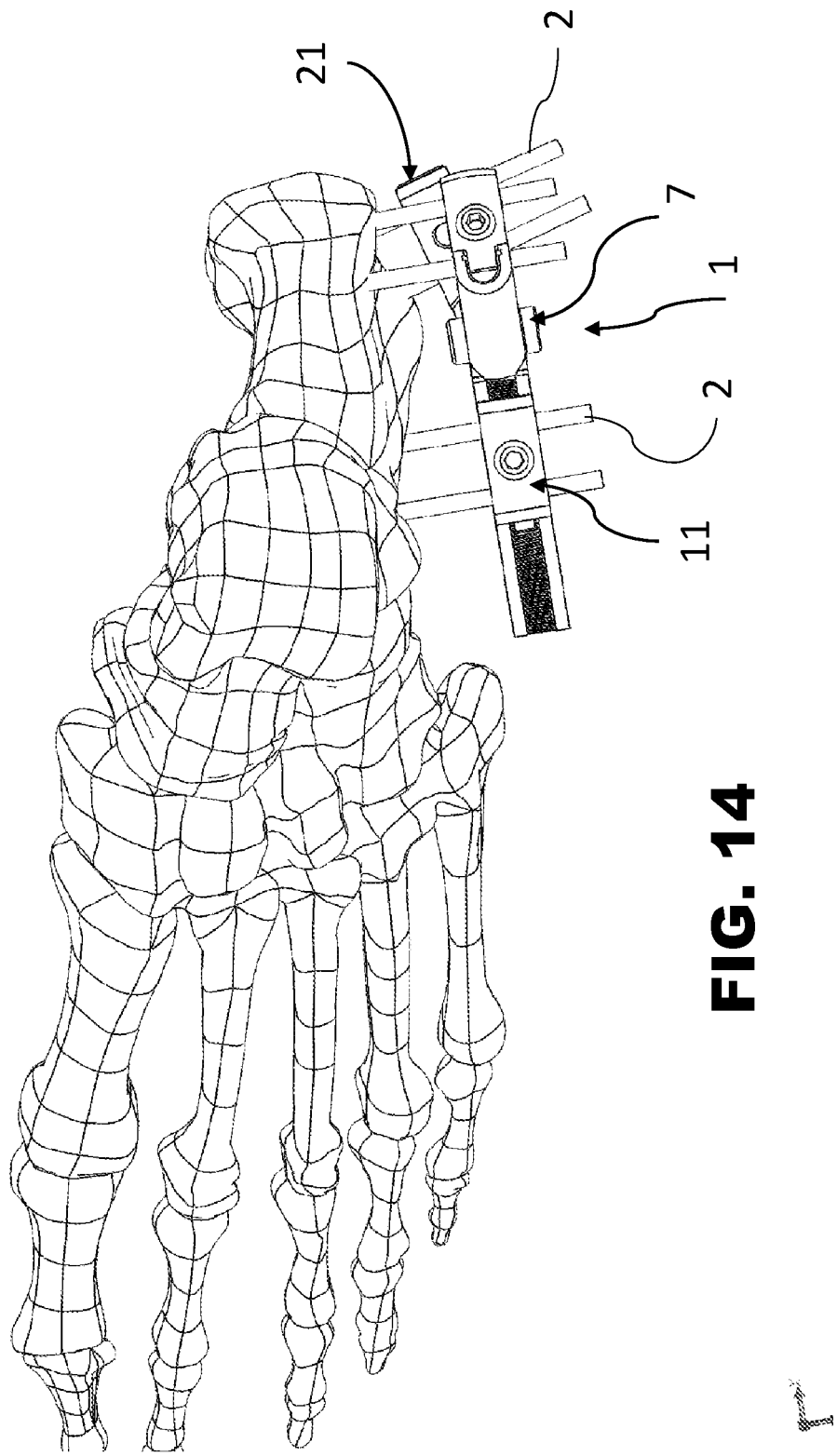
FIG. 14 shows a top view of the fixator of FIG. 1 applied to a calcaneus shown by schematic lines.

The cage 65 is shown in a perspective view in FIG. 13 and is structured with a spheroidal central portion 68 joined to two opposite truncated-cone portions 69 to adhere to the internal walls of the receiving seats 63, 64 and allow rotating the bone screw housed in said seats with predetermined angular excursion.

In a completely analogous way, even the other two clamps 21 and 31 have shaped seats with angular recesses to allow the bone screws 2 located more outside the fixator to be angularly movable with respect to an alignment transversal to the clamp of the innermost bone screw.

In FIG. 9 the shape of the elevated portion 39 of the "L"-shaped clamp is shown, which also has in this case as well a seat 71 for bone screw 2 conventionally configured as a semi-circular section channel whereas the other seat 72 is instead shaped with a semi-spherical central portion 73 and opposite angular recesses defined by the flared and semi-conical seats 74.

In FIG. 10 the shape of the base portion 20 of the second clamp 21 is shown, which has in this case as well a seat 81 for bone screw 2 conventionally configured as a semi-circular section channel whereas the other seat 82 is instead shaped with a semi-spherical central portion 83 and opposite angular recesses defined by the flared and semi-conical shaped seats 84.

Figure 11:
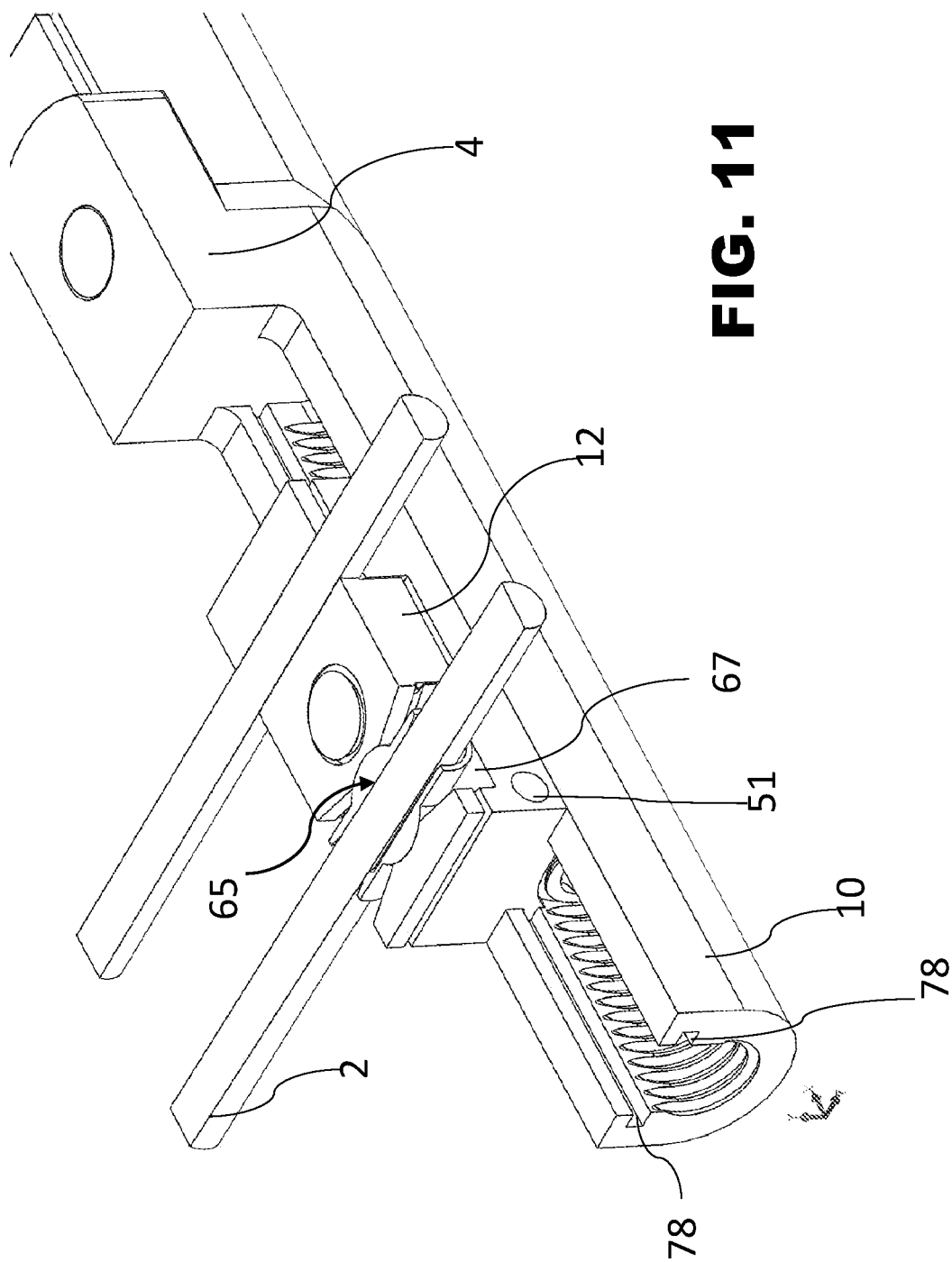

In FIG. 11 the base portion 12 of the first clamp is schematically shown with seats for the respective bone screws 2 joined to the seats of the lid shown in FIG. 8. In this figure the cage 65 is shown in section.

Let us now briefly see the operation and advantages of the orthopedic fixator 1 according to the present disclosure.

The fixator 1 offers a high mechanical stability due to the possibility of positioning and holding at least three distinct pairs of two bone screws 2, with each pair held by one of the respective clamps 11, 21 and 31.

The three pairs of bone screws 2 are intended to connect to each other, through the rigid structure of the body of the fixator 1, three different areas of the calcaneus close to each other.

As shown in FIG. 2, the fixator is easier to apply thanks to the possibility of an initial temporary positioning with K-wires, indicated with reference number 70, placed at the ends of the clamps in the respective holes 51, 52 and 53. These K-wires allow the fixator 1 to be temporarily fixed according to the orthopedic surgeon's judgment and do not interfere with the subsequent insertion of the final stabilization bone screws 2, being positioned at the extreme and peripheral dimensions of the fixator 1. The K-wires are removed upon insertion of the bone screws 2.

The structure of the fixator 1 allows at least two clamps to slide independently, the first 11 and the third 31 clamps mounted sliding on their respective supports 10 and 30.

The first clamp 11 is sliding on a substantially horizontal guide, extended along the X-X axis, whereas the third clamp is sliding on the oblique guide represented by the third support 30 extended along the Y-Y axis, which is oblique with respect to the previous one.

The lead screws 15 and/or 45, placed inside the tracks 10 and 30 supporting the respective sliders 12 and 32, allow the axial movement of the respective clamps and thus of the fragments of the fracture in order to generate preload on the fracture gap and a reconstruction of the calcaneal geometry. The particular elastic interference shape, thanks to suitable cuts in the end part of the thread of the lead screw, further allows friction of the screw itself, thus preventing the accidental unscrewing thereof.

Furthermore, the fixator 1 offers the possibility to orient the position of the second support 20 and of the related second side clamp 21 in the most adherent varus valgus position to the anatomy of the calcaneus, this arrangement is schematically shown in the top view of FIG. 12.

This possibility, along with that of orienting at least one of the two bone screws 2 with respect to the other, in particular the external screws held by the clamps, allow encountering the various anatomical sites with simplicity and safety.

With respect to the known solutions, the fixator 1 application technique is therefore facilitated due to the following factors:

the screws 15, 35 for moving the sliding clamps 11, 31 are also smaller in size than the current screws for moving the clamps, thus making the fixator body substantially transparent in radiographs;

the insertion of K-wires 70 allows delimiting the intervention field and keeping the position of the fixator stable, allowing the surgeon to check before inserting the bone screws 2;

the closure from below of the jaw lid 23 of the second clamp 21 favors the assembly in situ since the tilted third support that bears the upper clamp represents an encumbrance that would make it difficult to close the lid by means of a screw inserted on top;

the possibility of orienting the outermost bone screws to the fixator at the ends makes it easier to select the desired anatomical site.

The closure of the jaw lid 23 of the second clamp 21 by means of the tightening screw 24 inserted and operated from below in the through-hole 25 requires keeping the lid in position while closing the screw, thus avoiding the rotation of the second clamp. This has been solved with a particular shape of the lid which keeps the rotation stable during the closing phase.

It should also be noted that the possibility of adjusting the axial excursion of the screw carriages 15, 35, by laterally operating the respective Allen heads 6, 46, allows having a simple assembly phase and a stability in movement that is practically free of clearance.

The outermost bone screws 2 are orientable with an angular movement whose axis is contained in a cone of about 40°. Alternatively, even an angular movement on the same plane as the other innermost bone screw 2 to the fixator 1 is providable, with an angle of approximately ±20°, represented in FIG. 11 with a flat 67 supporting the ring nut 65 of the base 12; all this ensures application flexibility and system stability at the same time. Moreover, this configuration allows orienting the screws on a single plane parallel to the resting axis of the rigid support 10.

The clamps 11, 21, 31 are designed in such a way as to have the outermost bone screw of each clamp orientable, whereas the other innermost bone screw of the clamp has a fixed seat that is transversal to the clamp in order to ensure greater stability.

The fixator of the present disclosure makes it easy to identify the insertion position of the bone screws 2 in the respective clamp thanks to the visible part of the screw holder seat that is always accessible.

It should also be noted that to meet the need for greater X-ray visibility, an axial movement of the sliding clamps was opted for, offered by a screw carriage 15, 35 attached to the clamp itself and screwable into the nut screw seat of the respective support 10, 30. The use of aluminum for the carriage structure 15, 35 makes everything partially transparent to X-rays depending on the thickness and intensity of the rays. The fixator in this case is more radiolucent in the very area where the fractures are located.

By operating by screwing the carriages 15, 35 through the respective Allen heads 6, 46, by means of a control key, it is possible to adjust the movement along the guide of each sliding clamp, making the surgeon able to apply compression or distraction on the fracture gap and at the same time to restore the geometry of the calcaneus by regenerating the anatomical angles of reference.

The clamps 10, 30 are in any case guided on the profiles 16, 17 or 36, 37 of the respective supports 10, 30 ensuring stability during sliding. The shape of the clamp in fact has a longitudinal projection or tooth 77, highlighted in FIG. 9, which helps guiding the clamp but also mitigating the risk of clamp-rigid support disassembly due to bending stresses deriving from the screws. A pair of opposite teeth 77 is sliding in opposing grooves 78 visible in FIG. 11 and located above the nut screw longitudinal threading 14 of the rigid support 10.

The need to keep the clamps in position during application is achieved by generating a friction on the rotation of the screw carriages 15, 35. The friction obtained by means of the elastic-prong crown end 85 with and the elastic interference exerted thereby prevents the free rotation of the respective screw carriage 15, 35, so that it does not accidentally unscrew, losing the position or preload on the fracture gap.

The elastic interference exerted by the elastic-prong crown 85 is expressed towards the internal profile of the nut screw seat 16 or 36.

The dimensions of the fixator 1 are proportionate to the anatomical dimensions of the calcaneus, based on the clinical experiences so far conducted.

In understanding the scope of the present invention, the term "comprising" and its derivatives, as herein used, are intended as open terms that specify the presence of the features, elements, components, groups, whole numbers and/or specified steps, but do not exclude the presence of other features, elements, components, groups, whole numbers and/or specified steps. The foregoing also applies to words with similar meanings such as for instance the terms, "including", "having" and derivatives thereof. Moreover, the terms "part", "section", "portion", "member" or "element", when used in the singular, may have the double meaning of a single part or a plurality of parts unless otherwise specified.

It will also be understood that, though the terms "first" and "second" or "semi" may be herein used to describe various components, these components should not be limited by these terms. These terms are only used to distinguish a component from another.

Although only selected embodiments were chosen to illustrate the present invention, it will be clear to the skilled in the art from this disclosure that various changes and modifications may be performed without departing from the scope of the invention as defined in the appended claims.

The invention claimed is:

1. An external fixator for orthopedic use, in particular for treatment of calcaneus fractures, comprising:
   a first clamp for fixing bone screws;
   a second clamp;
   a third clamp;
   a rigid support for the first clamp;
   a second support for the second clamp, said second support being hinged at an end of the rigid support; and
   a third support for the third clamp, said third support being hinged at the end of the rigid support; and
   the rigid support being configured as at least one guide with the first clamp slidingly mounted thereon; wherein the end of the rigid support for connection with the second and third supports is configured to house respective hinges, wherein the rotational axes of said hinges are orthogonal to each other.

2. The fixator according to claim 1, wherein the third support is also configured as a guide with the third clamp sliding thereon.

3. The fixator according to claim 2, wherein the third clamp is mounted on an "L"-shaped element having a slider base side sliding on the third support and an elevated portion that is perpendicular to the base side whereon a jaw lid of the third clamp is coupled.

4. The fixator according to claim 1, wherein the at least one guide comprises two opposite guides and the rigid support has a U-shaped cross-section, with a bottom of the U shape provided with an internal longitudinal thread and open ends of the U shape provided with the opposite guides; and an externally threaded cylindrical carriage is slidable by screwing into the longitudinal thread of the rigid support.

5. The fixator according to claim 4, wherein the first clamp has a base with a portion that is projecting downwards to be held in an annular recess formed on said threaded cylindrical carriage and is further provided with at least one guide and anti-disassembly longitudinal tooth.

6. The fixator according to claim 4, wherein said cylindrical carriage is configured with a self-friction structure.

7. The fixator according to claim 1, wherein the rigid support and said second and third supports are made of radiolucent material, and the hinges are made of partially radiolucent material.

8. The fixator according to claim 1, wherein at least one of the first clamp, the second clamp, and the third clamp has a first seat for receiving a first bone screw and a second seat for receiving a second bone screw, the first seat having angular recesses to allow housing the first bone screw in a tilted manner with respect to the second bone screw that is transversally held by the clamp.

9. The fixator according to claim 8, wherein the first seat is positioned outwards with respect to the second seat.

10. The fixator according to claim 8, wherein the first seat allows orienting the screws on only one plane that is parallel to a resting axis of the rigid support.

11. The fixator according to claim 8, wherein the fixator comprises a cage element inserted in the first seat with angular recesses to guide and angularly orient the first bone screw into a corresponding angled seat of the clamp.

12. The fixator according to claim 1, wherein at least one of the first clamp, the second clamp, and the third clamp has a first seat and a second seat for receiving respective bone screws, the second seat being transversal and the first seat being tilted with respect to the second seat.

13. The fixator according to claim 1, wherein the second clamp has a base corresponding to the second support and a removable jaw lid that is mounted on the base by means of a tightening screw coupling.

14. The fixator according to claim 13, wherein said tightening screw is inserted in a threaded hole passing through the base and that a head of the tightening screw is hiddenly received into the base.

15. The fixator according to claim 1, wherein each clamp comprises a respective transversal through-hole placed at one end of the clamp towards the outside of the fixator to house a corresponding K-wire.

\* \* \* \* \*